(12) United States Patent
Gilbert

(10) Patent No.: US 8,568,400 B2
(45) Date of Patent: Oct. 29, 2013

(54) METHODS AND APPARATUS FOR SMART HANDSET DESIGN IN SURGICAL INSTRUMENTS

(75) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 592 days.

(21) Appl. No.: 12/565,103

(22) Filed: Sep. 23, 2009

(65) Prior Publication Data
US 2011/0071520 A1 Mar. 24, 2011

(51) Int. Cl.
*A61B 18/18* (2006.01)

(52) U.S. Cl.
USPC .................................. 606/34; 606/38; 606/42

(58) Field of Classification Search
USPC ......................................... 606/34, 38, 41, 42
See application file for complete search history.

(56) References Cited

U.S. PATENT DOCUMENTS

| | | | | |
|---|---|---|---|---|
| 3,875,945 A * | 4/1975 | Friedman | ........................ | 606/45 |
| 3,913,583 A * | 10/1975 | Bross | .............................. | 606/35 |
| 3,923,063 A * | 12/1975 | Andrews et al. | ................ | 606/38 |
| 4,196,734 A * | 4/1980 | Harris | .............................. | 606/31 |
| 5,400,267 A * | 3/1995 | Denen et al. | ..................... | 702/59 |
| 5,651,780 A * | 7/1997 | Jackson et al. | .................... | 606/1 |
| 6,402,743 B1* | 6/2002 | Orszulak et al. | ................ | 606/34 |
| 6,611,793 B1 | 8/2003 | Burnside | | |
| 6,979,987 B2* | 12/2005 | Kernahan et al. | ............. | 323/283 |
| 7,300,435 B2 | 11/2007 | Wham et al. | | |
| 7,883,458 B2* | 2/2011 | Hamel | .............................. | 600/1 |
| 2003/0208196 A1* | 11/2003 | Stone | ................................ | 606/41 |
| 2003/0233089 A1* | 12/2003 | Ohyama et al. | ................. | 606/46 |
| 2006/0206110 A1 | 9/2006 | Knowlton | | |
| 2007/0156125 A1* | 7/2007 | DeLonzor | ........................ | 606/21 |
| 2007/0167941 A1* | 7/2007 | Hamel et al. | ..................... | 606/34 |
| 2008/0147089 A1 | 6/2008 | Loh et al. | | |
| 2009/0248021 A1 | 10/2009 | McKenna | | |
| 2010/0049188 A1* | 2/2010 | Nelson et al. | .................... | 606/34 |
| 2010/0262139 A1* | 10/2010 | Beller et al. | ..................... | 606/41 |
| 2011/0130751 A1* | 6/2011 | Malis et al. | ...................... | 606/33 |
| 2012/0078278 A1* | 3/2012 | Bales et al. | ................... | 606/169 |

FOREIGN PATENT DOCUMENTS

| | | |
|---|---|---|
| WO | WO 2008142398 | 11/2008 |
| WO | WO 2009074329 | 6/2009 |
| WO | WO 2009137421 | 11/2009 |

OTHER PUBLICATIONS

International Search Report EP10178690 dated Jan. 21, 2011.

* cited by examiner

*Primary Examiner* — Linda Dvorak
*Assistant Examiner* — Jocelyn D Ram

(57) ABSTRACT

An electrosurgical instrument is provided which includes a housing and an electrocautery blade supported within the housing and extending distally. The housing has a treatment portion attached and defining a chamber therein for retaining an activation circuit and a control circuit. The activation circuit is operably coupled to at least one activation element that is activatable to control the delivery of electrosurgical energy from a generator to tissue proximate the treatment portion. The control circuit includes a microprocessor to enable bidirectional communication between the electrosurgical instrument and the generator relating to usage information of the electrosurgical instrument. The usage information includes serial number of the electrosurgical instrument, instrument type, number of times the electrosurgical instrument has been activated, overall time the electrosurgical instrument has been used, operating parameters of the at least one activation element during each activation, operational status of the treatment portion during each activation, and power settings.

12 Claims, 7 Drawing Sheets

METHODS AND APPARATUS FOR SMART HANDSET DESIGN IN SURGICAL INSTRUMENTS

BACKGROUND

1. Technical Field

The present disclosure relates generally to an electrosurgical system having a generator for generating radio-frequency (RF) power and an electrosurgical instrument configured for a two way communication with the generator to exchange data information therebetween.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical instrument, which transfer radio-frequency (RF) electrical energy to a tissue site. The electrosurgical energy is returned to the electrosurgical source via a return electrode pad positioned under a patient (e.g., a monopolar system configuration) or a smaller return electrode positionable in bodily contact with or immediately adjacent to the surgical site (e.g., in a bipolar system configuration). The waveforms produced by the RF source yield a predetermined electrosurgical effect known generally as electrosurgical cutting and fulguration.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned immediately adjacent the electrodes. When the electrodes are sufficiently separated from one another, the electrical circuit is open and thus inadvertent contact with body tissue with either of the separated electrodes does not cause current to flow.

In particular, electrosurgical fulguration includes the application of electric spark to biological tissue, for example, human flesh or the tissue of internal organs, without significant cutting. The spark is produced by bursts of radio-frequency electrical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical instrument" is intended to include instruments which have a handpiece that is attached to an active electrode and which is used to cauterize, coagulate and/or cut tissue. Typically, the electrosurgical instrument may be operated by a hand switch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical instrument is connected to a suitable electrosurgical energy source (i.e., generator) which produces the radio-frequency electrical energy necessary for the operation of the electrosurgical instrument. In general, when an operation is performed on a patient with an electrosurgical instrument, electrical energy from the electrosurgical generator is conducted through the active electrode to the tissue at the site of the operation and then through the patient to a return electrode. The return electrode is typically placed at a convenient place on the patients body and is attached to the generator by a conductive material. Typically, the surgeon activates the controls on the electrosurgical instrument to select the modes/waveforms to achieve a desired surgical effect. The "modes" relate to the various electrical waveforms, e.g., a cutting waveform has a tendency to cut tissue, a coagulating wave form has a tendency to coagulate tissue and a blend wave form is somewhere between a cut and coagulate waveform. The power or energy parameters are typically controlled from outside the sterile field which requires an intermediary like a circulating nurse to make such adjustment.

Electrosurgical generators have numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. However, conventional electrosurgical systems have one way communication from the generator to the electrosurgical instrument. A conventional electrosurgical instrument is a passive device. The generator typically performs any active query of the state of the switches, slider, device identification, etc., while the electrosurgical instrument has no computational or active processing capability.

Moreover, surgeons typically follow preset control parameters and stay within known modes and power settings. Further, some electrosurgical instruments are frequently recommended as "single use" instrument. To this end, during surgery, a surgeon may have to replace the electrosurgical instrument before completing the operation for various reasons, such as instrument failure. The new instrument, however, may not have current usage information that may aid the surgeon. For example, during surgery using the old instrument, the power intensity had to be adjusted to a higher level due to the unique tissue of the patient. This higher level of intensity typically would not be recognized by the new instrument.

SUMMARY

In general, it is an object of the present invention to provide a device and system to enable bidirectional communication between an electrosurgical instrument and a generator and a power circuit to enable the communications as well as any active processing in the electrosurgical instrument.

According to an aspect of the present disclosure an electrosurgical instrument is provided including an elongated housing. At least one electrocautery end effector is removably supported within the housing and extends distally from the housing. The electrocautery end effector is connected to a source of electrosurgical energy and a selector is supported on the housing for selecting a range setting of energy to be delivered from the source of electrosurgical energy to the at least one electrocautery end effector. In use, the selector is actuatable to select a range setting corresponding to a particular electrocautery end effector connected to the housing.

The housing has a treatment portion attached thereto and defines a chamber therein for retaining an activation circuit and a control circuit. The activation circuit is operably coupled to one or more activation elements that are activatable to control the delivery of electrosurgical energy from a generator to tissue proximate the treatment portion. Each activation element may be configured and adapted to selectively complete a control loop extending from the source of electrosurgical energy upon actuation thereof. In use, actuation of one of the activation switches produces tissue division with hemostatic effect at the electrocautery blade.

The control circuit includes a microprocessor or similar programmable device(s) (e.g., a PSOC, FPGA, PLA, PAL and the like) to enable bidirectional communication between the electrosurgical instrument and the generator relating to usage information of the electrosurgical instrument. The usage information is selected from the group consisting of serial number of the electrosurgical instrument, instrument type, number of times the electrosurgical instrument has been activated, overall time the electrosurgical instrument has been used, operating parameters of the at least one activation element during each activation, operational status of the treatment portion during each activation, and power settings.

The electrosurgical instrument may further include a control circuit supported in the housing. The control circuit may include a microprocessor or similar programmable device(s) (e.g., a PSOC, FPGA, PLA, PAL and the like) to control and enable bidirectional communication between the electro surgical instrument and storage/retrieval of usage information. The control circuit is electrically connected to the source of electrosurgical energy and record usage information of the instrument. The usage information may be retained at the electrosurgical instrument and downloaded to the generator in response to request signals from the generator. The usage information may include a serial number of the electrosurgical instrument, usage time of the electrosurgical instrument, voltage, power, current, and impedance.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Figure 1:
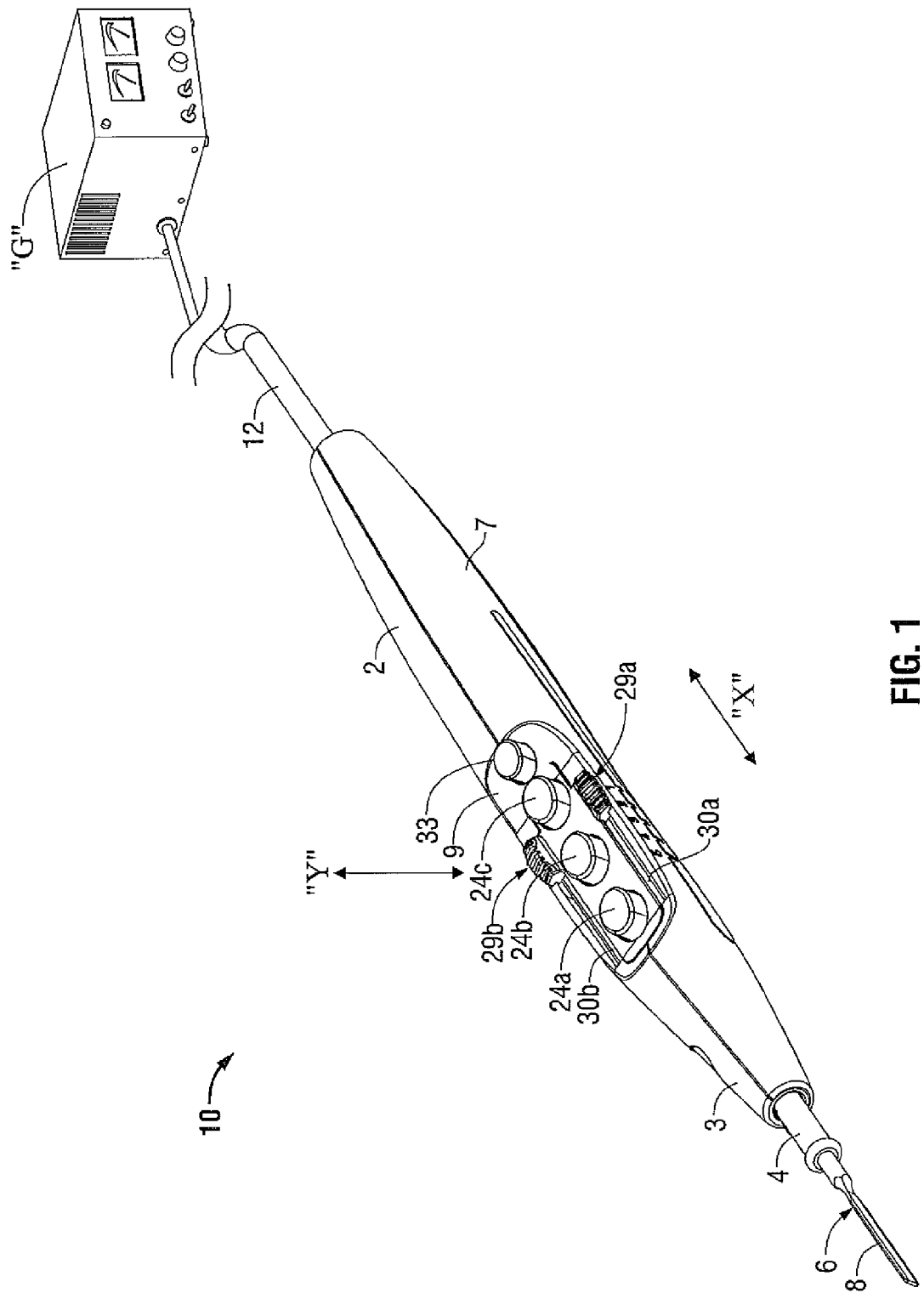
FIG. 1 is a perspective view of an electrosurgical instrument in accordance with one embodiment of the present disclosure.

Particular embodiments of the presently disclosed electrosurgical instrument (e.g., electrosurgical pencil) will now be described in detail with reference to the drawing figures wherein like reference numerals identify similar or identical elements.

As used herein, the term "distal" refers to that portion which is further from the user while the term "proximal" refers to that portion which is closer to the user or surgeon.

As used herein, the term "node" refers to portion for making electrical contact with a device, component, system, or semiconductor. For example, a node may be a connector, a soldered joint, and may be temporary or permanent.

FIG. 1 sets forth a perspective view of an electrosurgical instrument constructed in accordance with one embodiment of the present disclosure and generally referenced by numeral 10. While the following description will be directed towards electrosurgical instruments it is envisioned that the features and concepts (or portions thereof) of the present disclosure can be applied to any electrosurgical type instrument, e.g., forceps, suction coagulators, vessel sealers, etc. The electrosurgical type instrument may be monopolar or bipolar instruments.

Figure 2:
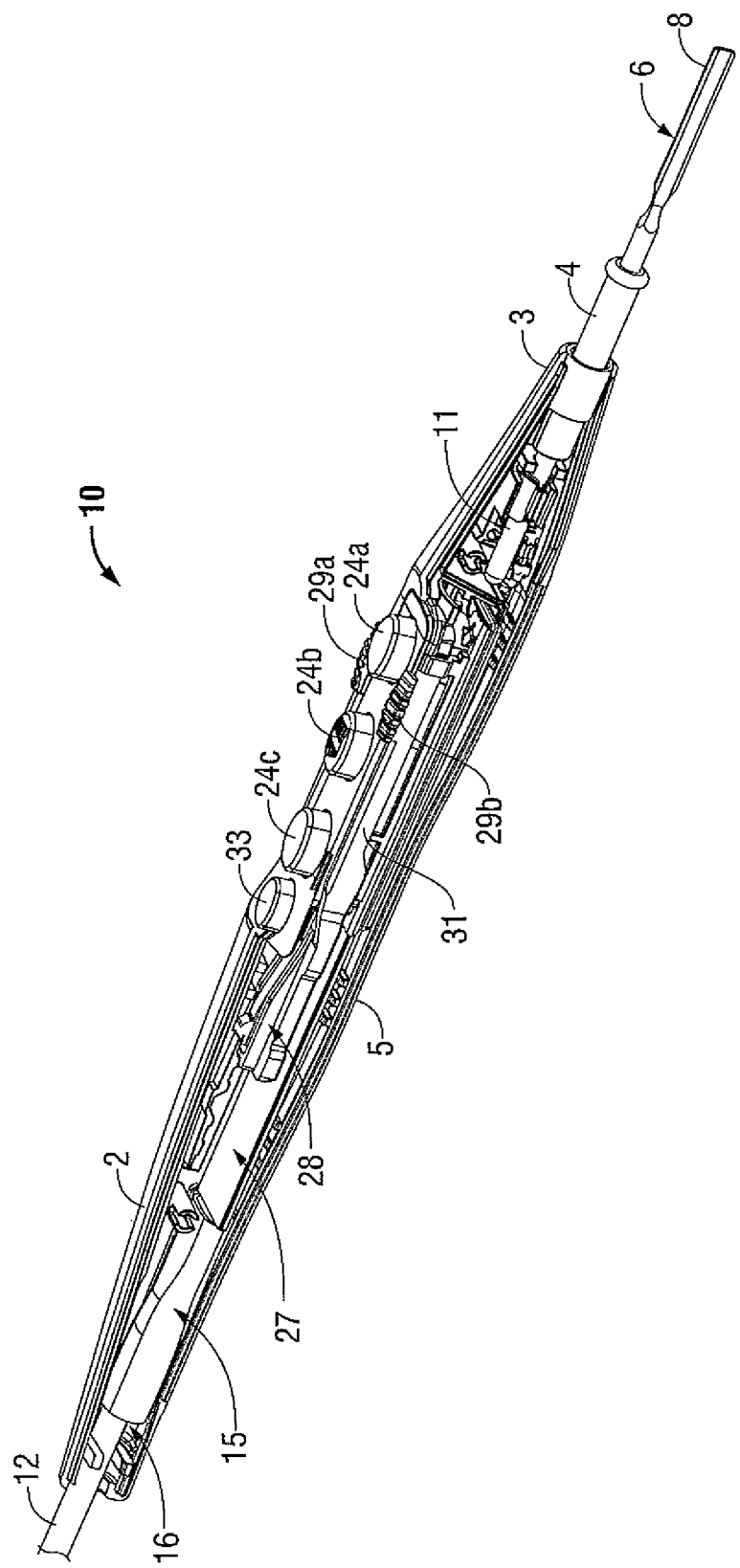
FIG. 2 is a partially broken away, perspective view of the electrosurgical instrument of FIG. 1.
Figure 3:
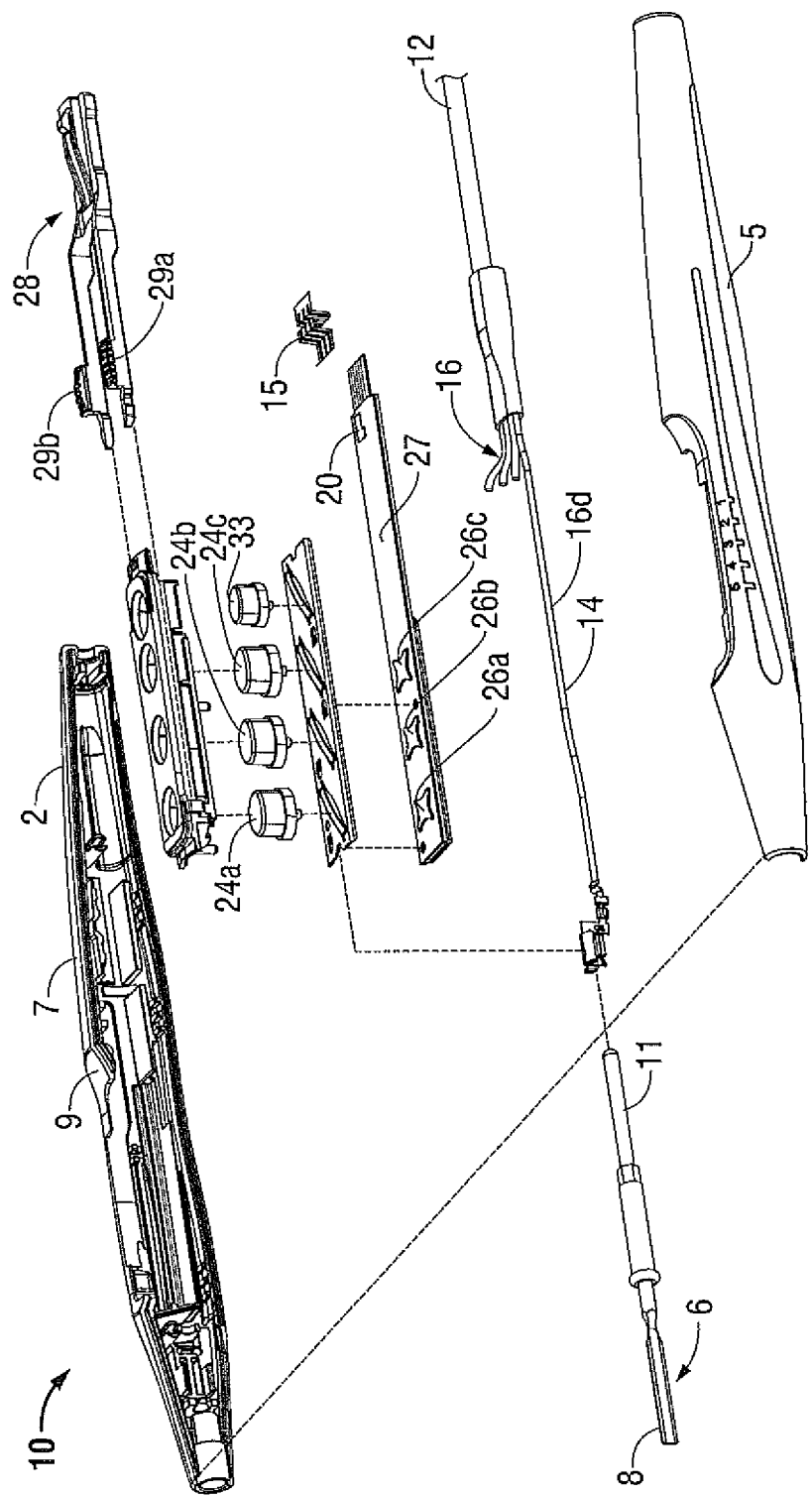
FIG. 3 is an exploded perspective view of the electrosurgical instrument of FIG. 1.

As seen in FIGS. 1-3, electrosurgical instrument 10 includes an elongated housing 2 configured and adapted to support a blade receptacle 4 at a distal end 3 thereof which, in turn, receives a replaceable electrocautery end effector 6 in the form of a loop and/or blade therein. Electrocautery blade 6 is understood to include a planar blade, a loop, a needle and the like. A distal end portion 8 of blade 6 extends distally from receptacle 4 while a proximal end portion 11 (see FIG. 3) of blade 6 is retained within distal end 3 of housing 2. Electrocautery blade 6 may be fabricated from a conductive type material, such as, for example, stainless steel, or may be coated with an electrically conductive material.

As shown, electrosurgical instrument 10 is coupled to a conventional electrosurgical generator "G" via a cable 12. Cable 12 includes a transmission wire 14 (see FIG. 3) that electrically interconnects electrosurgical generator "G" with proximal end portion 11 of electrocautery blade 6. Cable 12 further includes control wires 16 that electrically interconnect mode activation switches (as will be described in greater detail below), supported on an outer surface 7 of housing 2, with electrosurgical generator "G". For the purposes herein the terms "switch" or "switches" include electrical actuators, mechanical actuators, electromechanical actuators (rotatable actuators, pivotable actuators, toggle-like actuators, buttons, etc.) or optical actuators.

Turning back to FIGS. 1-3, as mentioned above, electrosurgical instrument 10 includes at least one activation switch, preferably three activation switches 24a-24c, each of which are supported on an outer surface 7 of housing 2. Each activation switch 24a-24c is operatively connected to a location on a tactile element 26a-26c (e.g., a snap-dome is shown) which, in turn, controls the transmission of RF electrical energy supplied from generator "G" to electrosurgical blade 6. More particularly, tactile elements 26a-26c are operatively coupled to a voltage divider network 27 (hereinafter "VDN 27") which forms a switch closure (e.g., here shown as a film-type potentiometer). For the purposes herein, the term "voltage divider network" relates to any known form of resistive, capacitive or inductive switch closure (or the like) that determines the output voltage across a voltage source (e.g., one of two impedances) connected in series. A "voltage divider" as used herein relates to a number of resistors connected in series that are provided with taps at certain points to make available a fixed or variable fraction of the applied voltage.

In use, depending on which activation switch 24a-24c is depressed a respective tactile elements 26a-26c is pressed into contact with VDN 27 and a characteristic signal is transmitted to electrosurgical generator "G" via control wires 16. Control wires 16 may be electrically connected to tactile elements 26a-26c via a node 15 (see FIGS. 2 and 3). By way of example only, electrosurgical generator "G" may be used in conjunction with the device wherein generator "G" includes a circuit for interpreting and responding to the VDN settings. However, the control circuit 20 includes a microprocessor 92 to control the bidirectional communications between the electrosurgical instrument 10 and electrosurgical generator "G" (as will be described in detail with references to FIGS. 4-9). In alternative embodiments, switches 24a-24c are electrically coupled to microprocessor 92 to receive the characteristic signals therefrom.

Activation switches 24a-24c are configured and adapted to control the mode and/or "waveform duty cycle" to achieve a desired surgical intent. For example, activation switch 24a can be set to deliver a characteristic signal to electrosurgical generator "G" which, in turn, transmits a duty cycle and/or waveform shape which produces a cutting and/or dissecting effect/function. Meanwhile, activation switch 24b can be set to deliver a characteristic signal to electrosurgical generator "G" which, in turn, transmits a duty cycle and/or waveform shape which produces a blending effect/function (e.g., a combination of a dissecting and a hemostatic effect/function). Activation switch 24c can be set to deliver a characteristic signal to electrosurgical generator "G" which, in turn, transmits a duty cycle and/or waveform shape which produces a hemostatic effect/function. Another activation switch 33 is electrically coupled to a microprocessor 92 to cause the microprocessor 92 to provide usage information to the generator "G".

The hemostatic effect/function can be defined as having waveforms with a duty cycle from about 1% to about 12%. The blending effect/function can be defined as having waveforms with a duty cycle from about 12% to about 75%. The cutting and/or dissecting effect/function can be defined as having waveforms with a duty cycle from about 75% to about 100%. It is important to note that these percentages are approximated and may be customized to deliver the desired surgical effect for various tissue types and characteristics.

Electrosurgical instrument 10 further includes an intensity controller 28 slidingly supported on housing 2. Intensity controller 28 includes a pair of nubs 29a-29b that are slidingly supported, one each, in respective guide channels 30a-30b, formed in outer surface 7 of housing 2 on either side of activations switches 24a-24c. By providing nubs 29a-29b on either side of activation switches 24a-24c, controller 28 can be easily manipulated by either hand of the user or the same electrosurgical instrument can be operated by a right-handed or a left-handed user.

Intensity controller 28 may be a slide potentiometer wherein nubs 29a-29b have a first position (e.g., proximal-most position closest to cable 12) corresponding to a relative low intensity setting, a second position (e.g., a distal-most position closest to electrocautery end effector 6) corresponding to a relative high intensity setting, and a plurality of intermediate positions corresponding to intermediate intensity settings. The intensity settings from proximal end to distal end may be reversed as well, e.g., high to low. Nubs 29a-29b of intensity controller 28 and corresponding guide channels 30a-30b may be provided with a series of cooperating discreet or dented positions defining a series of positions, preferably five, to allow easy selection of the output intensity from the low intensity setting to the high intensity setting. The series of cooperating discreet or dented positions also provide the surgeon with a degree of tactile feedback. As best seen in FIG. 2, intensity controller 28 can include a series of indicia 31 provided thereon which are visible through guide channels 30a-30b. Indicia 31 may be a series of numbers (e.g., numbers 1-5) that reflect the level of intensity that is to be transmitted. Alternatively, level indicators may be printed alongside the sides of guide channels 30a-30b along which nubs 29a-29b slide.

Intensity controller 28 is configured and adapted to adjust the power parameters (e.g., voltage, power and/or current intensity) and/or the power verses impedance curve shape to affect the perceived output intensity. For example, the greater intensity controller 28 is displaced in a distal direction the greater the level of the power parameters transmitted to electrocautery blade 6. Conceivably, current intensities can range from about 60 mA to about 240 mA when using an electrosurgical blade and having a typical tissue impedance of about 2K ohms. An intensity level of 60 mA provides very light and/or minimal cutting/dissecting/hemostatic effects. An intensity level of 240 mA provides very aggressive cutting/dissecting/hemostatic effects. Accordingly, the preferred range of current intensity is from about 100 mA to about 200 mA at 2K ohms.

The intensity settings may be preset and selected from a look-up table based on a choice of electrosurgical instruments/attachments, desired surgical effect, surgical specialty and/or surgeon preference. The selection may be made automatically or selected manually by the user. The intensity values may be predetermined or adjusted by the user.

In operation and depending on the particular electrosurgical function desired, the surgeon depresses one of activation switches 24a-24c, in the direction indicated by arrow "Y" (see FIG. 1) thereby urging a corresponding switch 26a-26c against VDN 27 and thereby controlling transmission of a respective characteristic signal to electrosurgical generator "G". For example, the surgeon can depress activation switch 24a to perform a cutting and/or dissecting function, activation switch 24b to perform a blending function, or activation switch 24c to perform a hemostatic function. In turn, generator "G" transmits an appropriate waveform output to electrocautery blade 6 via transmission wire 14.

In order to vary the intensity of the power parameters of electrosurgical instrument 10, the surgeon displaces intensity controller 28 in the direction indicated by double-headed arrow "X". As mentioned above, the intensity can be varied from approximately 60 mA for a light effect to approximately 240 mA for a more aggressive effect. For example, by positioning nubs 29a-29b of intensity controller 28 closer to the proximal-most end of guide channels 30a-30b (i.e., closer to cable 12) a lower intensity level is produced and by positioning nubs 29a-29b of intensity controller 28 closer to the distal-most end of guide channels 30a-30b (i.e., closer to electrocautery end effector 6) a larger intensity level is produced resulting in a more aggressive effect being produced. It is envisioned that when nubs 29a-29b of intensity controller 28 are positioned at the proximal-most end of guide channels 30a-30b, VDN 27 is set to a null and/or open position. Preferably, electrosurgical instrument 10 is shipped with intensity controller 28 set to the null and/or open positions.

As described above, intensity controller 28 can be configured and adapted to provide a degree of tactile feedback. Alternatively, audible feedback can be produced from intensity controller 28 (e.g., a "click"), from electrosurgical energy source "G" (e.g., a "tone") and/or from an auxiliary sound-producing device such as a buzzer (not shown).

As seen in FIGS. 1 and 3, intensity controller 28 and activation switches 24a-24c are supported in a recess 9 formed in outer wall 7 of housing 2. Desirably, activation switches 24a-24c are positioned at a location where the fingers of the surgeon would normally rest when electrosurgical instrument 10 is held in the hand of the surgeon while nubs 29a-29b of intensity controller 28 are placed at locations which would not be confused with activation switches 24a-24c. Alternatively, nubs 29a-29b of intensity controller 28 are positioned at locations where the fingers of the surgeon would normally rest when electrosurgical instrument 10 is held in the hand of the surgeon while activation switches 24a-24c are placed at locations which would not be confused with nubs 29a-29b of intensity controller 28. In addition, recess 9 formed in outer wall 7 of housing 2 advantageously minimizes inadvertent activation (e.g., depressing, sliding and/or manipulating) of activation switches 24a-24c and intensity controller 28 while in the surgical field and/or during the surgical procedure.

As seen in FIG. 3, electrosurgical instrument 10 includes a molded/contoured hand grip 5 that substantially surrounds the distal and proximal ends of housing 2 as well as the underside of housing 2. Contoured hand grip 5 is shaped and dimensioned to improve the handling of electrosurgical instrument 10 by the surgeon. Accordingly, less pressure and gripping force is required to use and/or operate electrosurgical instrument 10 thereby potentially reducing the fatigue experienced by the surgeon.

Figure 4:
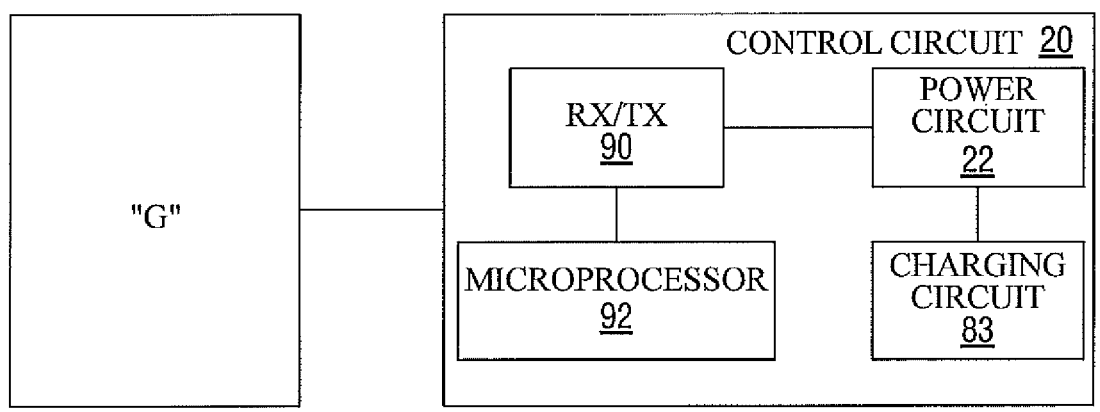
FIG. 4 is a block diagram of a control circuit for use with an instrument according to the present disclosure.

FIG. 4 is a block diagram of a control circuit 20 in accordance with the present disclosure. The control circuit 20 electrically connects to the source of electrosurgical energy via power cord 12 (see FIG. 3). The control circuit 20 may record usage information and enable bidirectional communication of the usage information between the electrosurgical instrument 10 and the generator "G". The usage information may include serial number of the electrosurgical instrument, instrument type, number of times the electrosurgical instrument has been activated, overall time the electrosurgical instrument has been used, operating parameters of the at least one activation element during each activation, operational status of the treatment portion during each activation, and power settings. The usage information may be transmitted to the generator "G" in real-time via cable cord 12 or may be retrievably stored to be transmitted to generator "G". Alternatively, the bidirectional or 2-way communication may be performed wirelessly by RF or inductive coupling or an optical sensor (sec FIG. 6). The usage information may be used for quality assurance purposes. For example, the usage information may serve as a feedback mechanism for a surgeon to increase or decrease the intensity level by adjusting the intensity controller 28 (FIG. 3) to achieve optimum cutting and fulguration. The usage information may also assist the electrosurgical instrument manufacturer to design a better instrument.

The control circuit 20 includes a power circuit 22 to supply power to the control circuit 20, transceiver 90 to enable bidirectional communication between control circuit 20 and generator "G" and a charging circuit 83 for charging energy source 82 (see FIG. 8) in order to provide backup power to control circuit 20.

Figure 5:
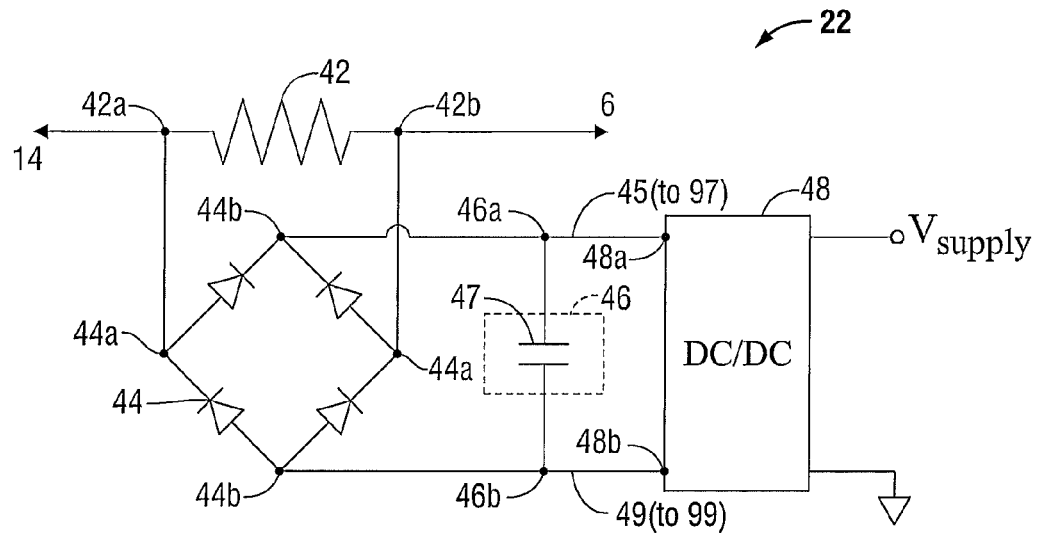
FIG. 5 is a schematic illustration of a power circuit for use with a control circuit according to the present disclosure.

FIG. 5 illustrates one embodiment of power circuit 22 used to power control circuit 20. Power circuit 22 includes a resistor 42 having first and second nodes 42a-42b. The first node 42a is electrically coupled to the source of electrosurgical energy (e.g., generator "G") via a transmission wire 14 and the second node 42b is electrically coupled to the electrocautery electrode 6. In alternative embodiments, node 42a may be connected to transmission wire 14 and node 42b may be connected to a ground, e.g., earth ground, chassis ground, or a return path and/or a ground to the generator "G". A first voltage difference is provided between the first and second nodes 42a-42b when the electrosurgical energy flows through the resistor 42. A bridge circuit 44 includes input and output node pairs 44a-44b, respectively. The input node pair 44a is electrically coupled to the first and second nodes 42a-42b of the resistor 42 to receive the first voltage difference. The bridge circuit 44 rectifies the first voltage difference to provide a second voltage.

A filter circuit 46 is included that has input and output node pairs 46a-46b. The input node pair 46a-46b of the filter circuit 46 is electrically coupled to the output node pair 44b of the bridge circuit 44 to receive the second voltage. The filter circuit 46 filters the second voltage to provide a third voltage. The third voltage may be considered an unregulated DC voltage signal. The filter circuit 46 may also include at least one capacitor 47 and a switched-mode power supply 48 that includes input and output node pairs 48a-48b. The input node pair 48a-48b of the switched-mode power supply 48 is electrically coupled to the output node pair 46a-46b of the filter circuit 46. The switched-mode power supply 48 receives the third voltage and provides a regulated voltage $V_{Supply}$ to supply power to the control circuit 20. The switched-mode power supply 48 may be a buck-boost power supply.

It should be understood that even though diodes are used as (as shown in bridge circuit 44 of FIG. 5 and bridge circuit 60 of FIG. 6) rectifiers made of solid state diodes, vacuum tube diodes, mercury are valves, metal-oxide-semiconductor transistor (MOSFET), and other components can be used to convert alternating current (AC) to direct current (DC).

Figure 6:
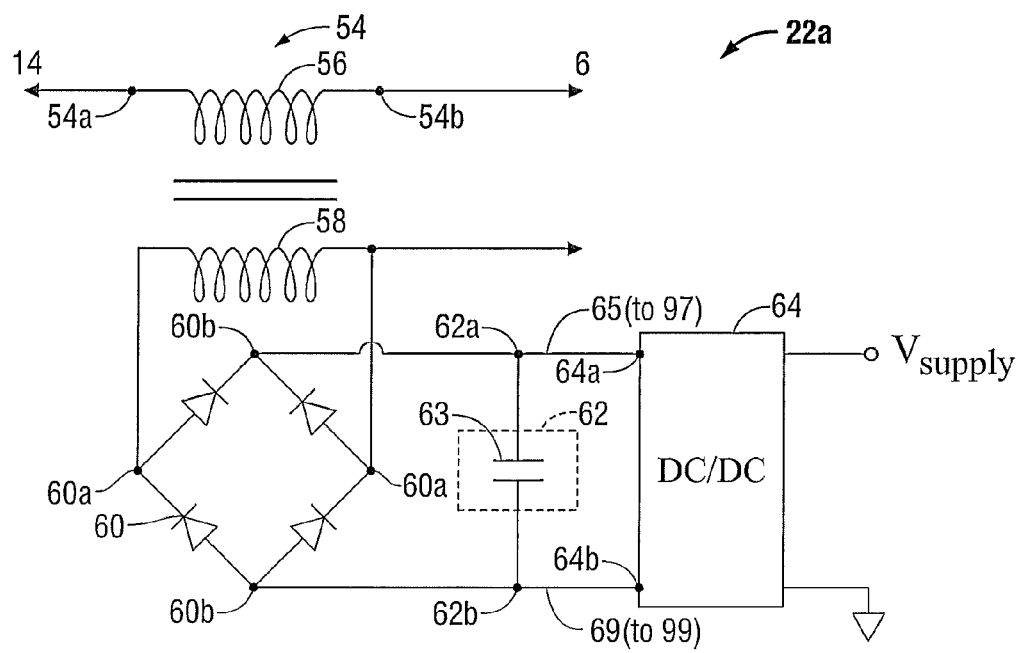
FIG. 6 is a schematic view of another embodiment of a power circuit for use with a control circuit according to the present disclosure.

FIG. 6 is a schematic illustration of the power circuit 22a used to power control circuit 20 in accordance with another embodiment of the present disclosure. The power circuit 22 of FIG. 6 uses an isolation barrier as a means of powering the control circuit 20. The power circuit 22 includes a transformer 54 with primary and secondary windings 56 and 58. A first node 54a of the primary winding 56 is electrically coupled to the source of electrosurgical energy (Generator "G") via transmission wire 14 and a second node 54b of the primary winding 56 is electrically coupled to the electrocautery electrode 6. The electrosurgical energy flowing through the primary winding 56 provides a first voltage across the secondary winding 58. Although FIG. 6 depicts an iron core transformer, an air core transformer may also be used. A bridge circuit 60 is included that has input and output node pairs 60a-60b. The input node pair 60a is electrically coupled to the secondary winding 58 of the transformer 54 to receive the first voltage. The bridge circuit 60 rectifies the first voltage to provide a second voltage.

A filter circuit 62 is included that has input and output node pairs 62a-62b. The input node pair 62a-62b is electrically coupled to the output node pair 60b of the bridge circuit 60 and is configured to receive the second voltage. The filter circuit 62 filters the second voltage to provide a third voltage. The filter circuit 62 may include one or more capacitors 63. A switched-mode power supply 64 is also included that has both input and output node pairs 64a-64b, the input node pair 64a-64b being electrically coupled to the output node pair 62a-62b of the filter circuit 62. The switched-mode power supply 64 receives the third voltage and provides a regulated voltage $V_{Supply}$ to supply power to the control circuit 20.

Figure 7:
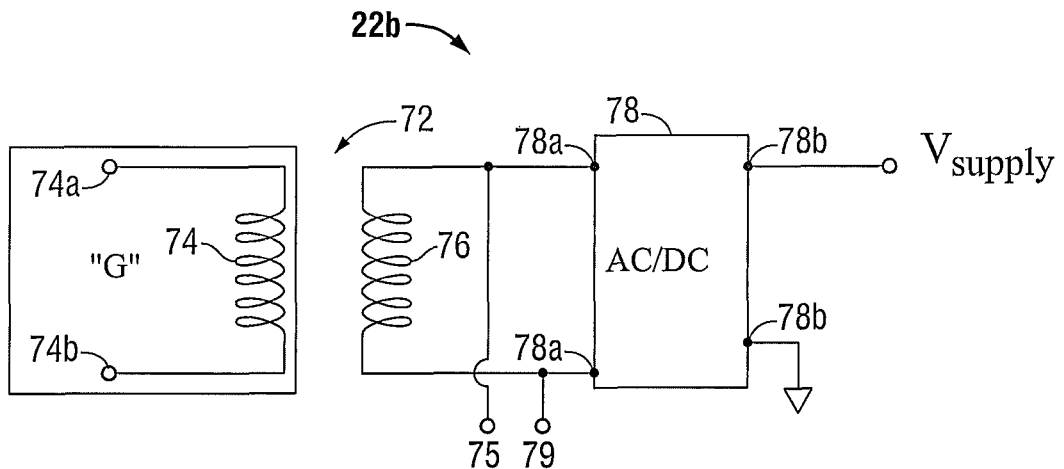
FIG. 7 is a schematic view of another embodiment of a power circuit for use with a control circuit according to the present disclosure.

FIG. 7 is a schematic illustration of power circuit 22b in accordance with yet another embodiment of the present disclosure. The power circuit 22 includes a transformer having primary and secondary windings 74 and 76. Primary winding 74 is electrically coupled to the source of switched energy (e.g., generator "G"), which may be a forward converter or other switched source via nodes 74a and 74b through transmission wires 6, 14. The switched energy flowing through the primary winding 74 provides a first voltage across the secondary winding 76. Although FIG. 7 depicts an air core transformer, an iron core transformer may also be used. Power circuit 22 further includes an AC-to-DC module 78 which has input and output node pairs 78a-78b, the input node pair 78a being electrically coupled to the secondary winding 76 of the transformer 72 to receive the first voltage. The AC-to-DC module 78 provides a DC voltage signal $V_{Supply}$ from the first voltage to supply power to the control circuit 20.

Figure 8:
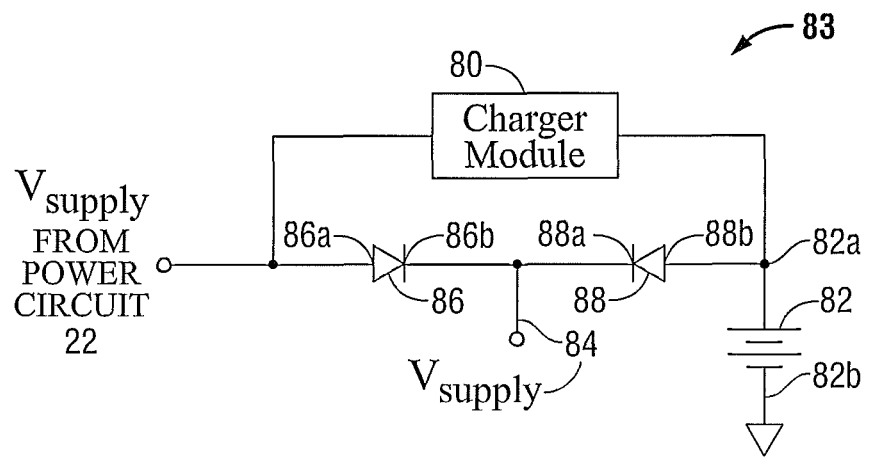
FIG. 8 is a schematic view of a charging circuit for use with the control circuit according to the present disclosure.

FIG. 8 is an embodiment of a charging circuit 83 which may optionally be implemented in the control circuit 20 of the present invention in order to supply backup power thereto. In use it is contemplated that it may be desirous to incorporate charging circuit 83 to recharge an energy device 82, which supplies back-up power to the control circuit 20, particularly during periods when the electrosurgical instrument 10 (FIG. 1) is not being activated by the end user. Energy device 82 includes positive and negative nodes 82a-82b, the negative node 82b being electrically coupled to a ground. The energy device 82 may be a battery and/or a supercapacitor. A charger module 80 is electrically coupled to the output voltage $V_{Supply}$ of power circuit 22 and to positive node 82a of the energy device 82 to provide a charging voltage to positive node 82a of the energy device 82. The charger module 80 may be a trickle charger and/or a constant-current constant-voltage recharger module (sometimes referred to as a "CCCV"). In instances where the power circuit 22 is configured to supply power to control circuit 20 during periods when the active electrode 6 (FIGS. 1-3) is activated (e.g., FIGS. 5 and 6), the charger module 80 may be able to simultaneously recharge the energy device 82 during such activation periods. A power supply node 84 is also electrically coupled to the energy device 82 and the output voltage signal $V_{Supply}$ from the power circuit 22 to supply energy ($V_{Supply'}$) to control circuit 20.

The charging circuit 83 also includes a first diode 86, which has anode and cathode nodes, the anode node 86a being electrically coupled to the voltage signal $V_{Supply}$ of the power circuit 22. The cathode node 86b of the first diode 86 is electrically coupled to the power supply node 84. A second diode 88 is also included that has anode and cathode nodes 88a-88b, the anode node 88b being electrically coupled to the energy device 82 and the cathode node 88a being electrically coupled to the power supply node 84.

Figure 9:
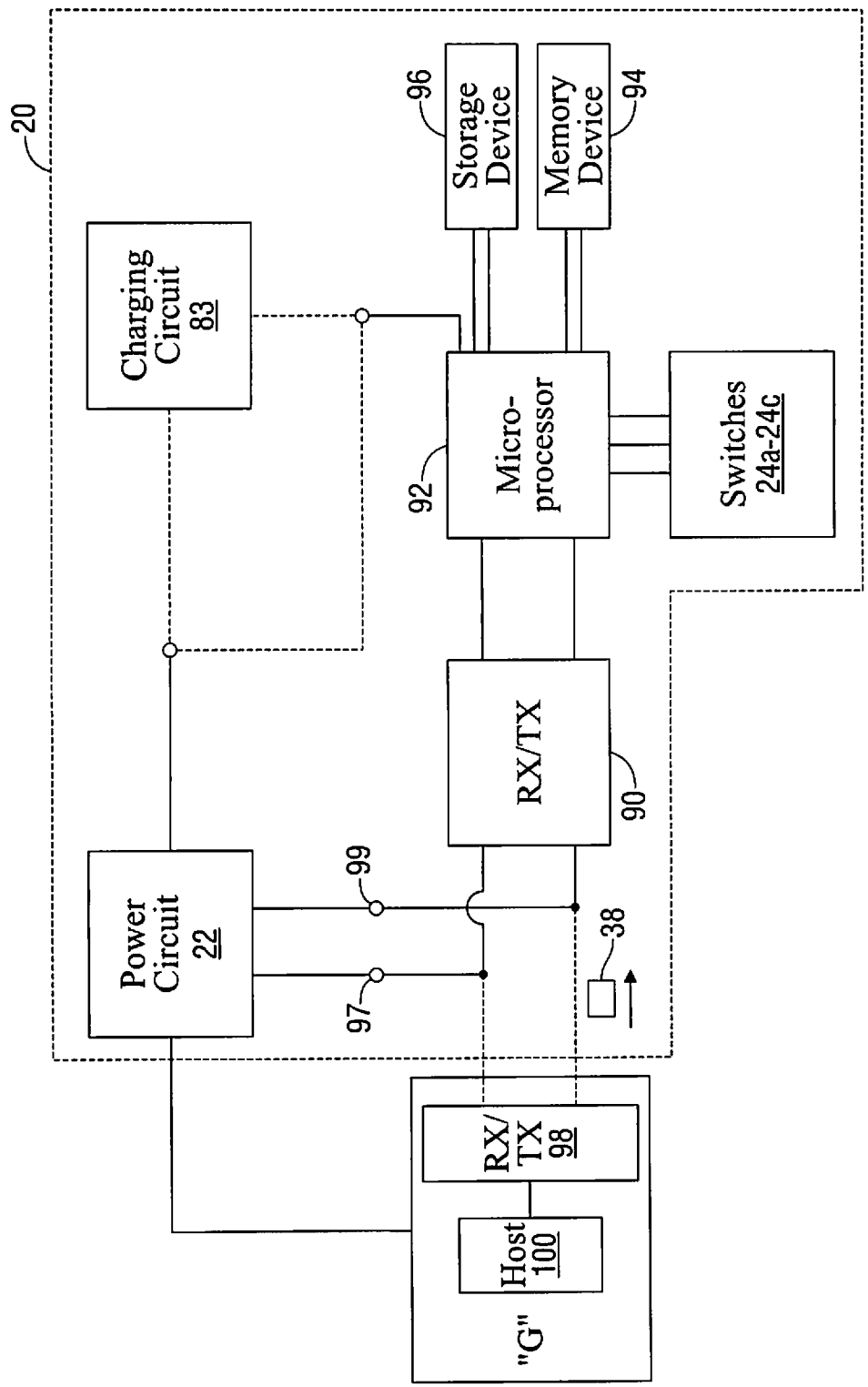
FIG. 9 is a schematic view of a control circuit according to the present disclosure.

FIG. 9 is schematic view of one embodiment of control circuit 20 according to the present disclosure. Control circuit 20 includes power circuit 22, optional charging circuit 83 and receiver/transmitter module 90. The receiver/transmitter module 90 may communicate bidirectionally with a host module of the generator "G". A microprocessor 92 is electrically coupled to the receiver/transmitter module 90 to operatively communicate with the host module of the generator "G" and the plurality of activation switches 24a-24c. The microprocessor 92 may be an AVR32 32-bit RISC processor manufactured by Atmel Corporation of San Jose, Calif., a MSP430 16-bit RISC processor manufactured by Texas Instruments of Dallas, Tex., or other low power processors.

A memory device 94 is electrically coupled to the microprocessor 92 and may store usage information. The memory device 94 may be an electrically erasable programmable read-only memory. A storage device 96 is electrically coupled to the microprocessor 92 and may store at least the serial number of the electrosurgical instrument. In another embodiment, the memory device 94 may be internal to the microprocessor 92, such as a flash memory.

The generator "G" includes a receiver/transmitter module 98 that is either optically coupled to a host module 100 of the generator "G" or, if the power circuit of FIG. 7 is used, may be inductively coupled by transformer 72 of FIG. 7, to communicate bidirectionally with the electrosurgical instrument 10. The optical coupling may utilize photodiode, phototransistors, photo-isolation, optocouplers, and the like. The inductive coupling may combine Pulse-width modulation (PWM) for AC/DC conversion with the receiver/transmitter serial data. The transformer 72 may be used for power PWM waveforms or the optics dispensed with and by combining PWM with the serial data on a carrier. The microprocessor 92 is electrically coupled to the receiver/transmitter module 90 to operatively communicate with the host module 100 of the generator "G" and the plurality of activation switches 24a-24c.

At the beginning of an operation, the surgeon may connect the electrosurgical instrument 10 to the generator "G" via cord 12. During surgery, the electrosurgical instrument 10 may track and store the usage information in the storage device 96. The generator "G" may send signal requests 38 to the control circuit 20 during surgery to request usage information of the electrosurgical instrument 10. In response to receiving the signal requests 38, the electrosurgical instrument 10 sends the stored usage information to a storage device (not shown) in the generator. In an event the instrument 10 does not respond to the request signals 38, the surgeon may switch the instrument 10 for another instrument. In another example, the electrosurgical instrument 10 may send the usage information to the generator "G" on its own volition without the signal requests 38. For example, if electrosurgical instrument 10 reaches a maximum threshold of the number of time the instrument has been activated and/or the overall time the instrument has been used, the instrument 10 may send the usage information to the generator automatically. A surgeon may then decide to dispose of the instrument 10 in favor of another instrument.

When the surgeon switches the electrosurgical instrument 10 in favor of another instrument, the most recent usage information stored in the generator must now be uploaded to the new instrument so that surgery may continue without a loss of information, for example, power control settings, intensity settings, etc. Before the download of usage information, the cable 12 of the original instrument 10 is disconnected from the generator "G". Another electrosurgical instrument is then connected to the generator "G'. Once the new instrument is connected and activated, the control circuit 20 enables bidirectional communication between the generator and the new instrument. As part of the bidirectional communication, the generator "G" sends usage information to the new instrument.

The stored usage information at the generator "G" may be useful for other purposes, such as quality assurance purposes. For example, the usage information may be used to improve development of future electrosurgical instruments including better default settings of operating parameters for future surgery. For example, the default voltage setting may be increased/decreased to optimize tissue ablation of a particular tissue type.

The circuit 20 includes a first node 97 and a second node 99. The first node 97 may be electrically coupled to a node 45 (FIG. 5) and the second node 99 may be electrically coupled to a node 49 (FIG. 5). Similarly, the first node 97 may be electrically connected to a node 65 (FIG. 6) and the second node 99 may be electrically coupled to a node 69 (FIG. 6). Finally, the first node 97 may be electrically coupled to a node 75 (FIG. 7) and the second node 99 may be electrically coupled to a node 79 (FIG. 7). In the case of the circuit 20 being electrically connected to a power circuit 22 as shown in FIGS. 5 and 6, data would be transmitted and received using a small μA amount of pulsed current at a carrier frequency substantially different than the RF frequency. The RF frequency would be filtered leaving data.

As described with reference to FIG. 8, charging circuit 83 may be optional, depending on the configuration of power circuit 22. In instances where charging circuit 83 may be required, such as where the output of power circuit 22 powers the control circuit 20 when the active electrode is activated (e.g., FIGS. 5, 6), power circuit 22 may connect to the power input of microprocessor 92 through charging circuit 83. If a back-up power source is not required, charging circuit 83 may be omitted, and power circuit 22 may connect directly to microprocessor 92.

It should be understood that the various components (e.g., transformer 72) shown within the control circuit 20 may be wholly or partially disposed within the electrosurgical instrument. For example, various components may be located on the generator "G" instead of the control circuit 20 (e.g., the transformer 72, bridge 60, and filter 62 may be included in the generator "G" instead of the control circuit 20).

It should also be understood that various alternatives and modifications could be devised by those skilled in the art. The present disclosure is intended to embrace all such alternatives, modifications and variances that fall within the scope of the appended claims.

The invention claimed is:

1. An electrosurgical instrument, comprising:
   a housing having a treatment portion attached thereto and defining a chamber therein for retaining an activation circuit and a control circuit, the activation circuit being operably coupled to at least one activation element that is activatable to control the delivery of electrosurgical energy from a generator to tissue proximate the treatment portion, the control circuit including:
      a power circuit including a filter circuit having input and output node pairs for receiving and transmitting at least one voltage signal, wherein a voltage output signal transmitted from the filter circuit processed to provide a regulated voltage to power to the control circuit;
      a microprocessor;
      a receiver/transmitter module coupled to the output node pair of the filter circuit and the microprocessor to enable bidirectional communication between the electrosurgical instrument and the generator relating to usage information of the electrosurgical instrument, the usage information being selected from the group consisting of serial number of the electrosurgical instrument, instrument type, number of times the electrosurgical instrument has been activated, overall time the electrosurgical instrument has been used, operating parameters of the at least one activation element during each activation, operational status of the treatment portion during each activation, and power settings; and
      a charging circuit including at least one first diode electrically coupled to the regulated voltage and at least one second diode electrically coupled to an energy device of the charging circuit for recharging the energy device for supplying back-up power to the control circuit during periods when the electrosurgical instrument is not activated.

2. The electrosurgical instrument according to claim 1, wherein the control circuit includes an electrically erasable programmable read-only memory, the electrically erasable programmable read-only memory is configured to store the usage information.

3. The electrosurgical instrument according to claim 1, wherein the receiver/transmitter module is configured to communicate bidirectionally with the generator in a. wireless manner via inductive coupling, the bidirectional communication includes the usage information being transmitted to the generator in real-time.

4. The electrosurgical instrument according to claim 1, wherein the receiver/transmitter module is configured to communicate bidirectionally with the generator in a wireless manner via an optical sensor, the bidirectional communication includes the usage information being transmitted to the generator in real-time.

5. The electrosurgical instrument according to claim 1, further including at least one additional activation element actuatable to cause the microprocessor to provide the usage information to the generator.

6. The electrosurgical instrument according to claim 1, wherein the power circuit includes:
   a resistor having first and second nodes, wherein the first node is electrically coupled to the generator and the second node is electrically coupled to the treatment portion, a first voltage difference is provided between the first and second nodes when electrosurgical energy flows through the resistor;
   a bridge circuit having input and output node pairs, the input node pair being electrically coupled to the first and second nodes of the resistor and configured to receive the first voltage difference, the bridge circuit configured to rectify the first voltage difference to provide a second voltage,
   wherein the input node pair of the filter circuit is electrically coupled to the output node pair of the bridge circuit to receive the second voltage, and the filter circuit is configured to filter the second voltage to provide a third voltage; and
   a switched-mode power supply having input and output node pairs, the input node pair of the switched-mode power supply being electrically coupled to the output node pair of the filter circuit, the switched-inside power supply configured to receive the third voltage and provide the regulated voltage to supply power to the control circuit.

7. The electrosurgical instrument according to claim 6, wherein the switched-mode power supply is a buck-boost power supply.

8. The electrosurgical instrument according to claim 6, wherein the filter circuit includes at least one capacitor electrically coupled to the input node pair of the filter circuit.

9. A method for making an electrosurgical instrument, comprising the steps of:
   providing a housing having a treatment portion attached thereto and defining a chamber therein to retain an activation circuit and a control circuit;
   operably coupling the activation circuit to at least one activation element that is activatable for controlling the delivery of electro surgical energy from a generator to tissue, the control circuit including:

a power circuit including a filter circuit having input and output node pairs for receiving and transmitting at least one voltage signal, wherein a voltage output signal transmitted from the filter circuit is processed to provide a regulated voltage to power to the control circuit;

a microprocessor;

a receiver/transmitter module coupled to the output node pair of the filter circuit and the microprocessor to enable bidirectional communication between the electrosurgical instrument and the generator relating to usage information of the electrosurgical instrument, the usage information being selected from the group consisting of serial number of the electrosurgical instrument, instrument type, number of times the electrosurgical instrument has been activated, overall time the electrosurgical instrument has been used, operating parameters of the at least one activation element during each activation, operational status of the treatment portion during each activation, and power settings; and a charging circuit including at least one first diode electrically coupled to the regulated voltage and at least one second diode electrically coupled to an energy device of the charging circuit for recharging the energy device for supplying back-up power to the control circuit during periods when the electrosurgical instrument is not activated.

10. The method as set forth in claim 9, further including recording and storing the usage information within the generator.

11. The method as set forth in claim 9, further including enabling bidirectional communication between the receiver/transmitter and the generator in a wireless manner, wherein the bidirectional communication includes transmitting the usage information to the generator in real-time.

12. The method as set forth in claim 9, further including: providing a the power circuit with:

a resistor having first and second nodes, wherein the first node is electrically coupled to the generator and the second node is electrically coupled to the treatment portion, a first voltage difference is provided between the first and second nodes when electrosurgical energy flows through the resistor;

a bridge circuit having input and output node pairs, the input node pair being electrically coupled to the first and second nodes of the resistor for receiving the first voltage difference, the bridge circuit rectifies the first voltage difference to provide a second voltage, wherein the input node pair of the filter circuit is electrically coupled to the output node pair of the bridge circuit to receive the second voltage, and the filter circuit filters the second voltage to provide a third voltage; and a switched-mode power supply having input and output node pairs, the input node pair of the switched-mode power supply being electrically coupled to the output node pair of the filter circuit, the switched-mode power supply receives the third voltage and provides the regulated voltage to supply power to the control circuit.

\* \* \* \* \*